United States Patent [19]

LaBombard et al.

[11] Patent Number: 5,529,727
[45] Date of Patent: Jun. 25, 1996

[54] METHOD OF TREATING CONTACT LENSES

[75] Inventors: Denis LaBombard, Georgetown; Jeanne Y. Ellis, Lynnfield, both of Mass.

[73] Assignee: Bausch & Lomb Incorporated, N.Y.

[21] Appl. No.: 278,086

[22] Filed: Jul. 20, 1994

[51] Int. Cl.$^6$ .................................................. B29D 11/00
[52] U.S. Cl. .......................... 264/1.36; 264/2.6; 264/446; 264/488
[58] Field of Search ................................ 264/1.36, 1.38, 264/22, 2.6, 446, 488

[56] References Cited

U.S. PATENT DOCUMENTS

| | | | |
|---|---|---|---|
| 3,822,196 | 7/1974 | O'Driscoll et al. | 264/1.36 |
| 3,915,609 | 10/1975 | Robinson | 264/1.36 |
| 3,916,033 | 10/1975 | Merrill. | |
| 4,152,508 | 5/1979 | Ellis | 526/279 |
| 4,330,383 | 5/1982 | Ellis. | |
| 4,686,267 | 8/1987 | Ellis | 526/245 |
| 4,780,515 | 10/1988 | Deichert | 526/245 |
| 4,826,889 | 5/1989 | Ellis et al. | 264/1.36 |
| 4,874,562 | 10/1989 | Hyon et al. | 264/1.36 |
| 5,135,297 | 8/1992 | Valint. | |

FOREIGN PATENT DOCUMENTS

| | | |
|---|---|---|
| 0108661A1 | 5/1984 | European Pat. Off.. |
| 0374590A2 | 6/1990 | European Pat. Off.. |
| 0374590A3 | 6/1990 | European Pat. Off.. |
| 0544926A1 | 6/1993 | European Pat. Off.. |

*Primary Examiner*—Mathieu D. Vargot
*Attorney, Agent, or Firm*—Edward W. Black; John E. Thomas; Craig E. Larson

[57] ABSTRACT

A method for treating contact lenses involves irradiation of the contact lens with high energy radiation while immersed in an aqueous medium such as saline solution.

15 Claims, No Drawings

METHOD OF TREATING CONTACT LENSES

BACKGROUND OF THE INVENTION

The present invention relates to a method of treating RGP contact lenses. The method is useful for sterilizing, improving dimensional stability and/or increasing surface wettability of the treated contact lens.

An effective method for improving dimensional stability of RGP contact lens materials, and especially contact lens materials formed of a rigid, gas permeable (RGP) copolymer, involves exposing the material to high energy radiation whereby the amount of excess, unreacted monomer in the material is reduced. U.S. Pat. No. 4,330,383 (Ellis et al.) discloses such a method wherein a polymeric contact lens material is exposed to high energy radiation to reduce the amount of unreacted monomer and improve dimensional stability of the material. The polymeric materials may be provided in the form of rods or buttons, which are subsequently irradiated and cut into contact lenses, or the polymeric material may be polymerized directly in a mold to form contact lenses. The irradiation process is preferably carried out at room temperature in an inert atmosphere.

In addition, various treatment methods have been proposed for increasing surface wettability or modifying surface properties of contact lenses.

Several methods involve grafting or covalently bonding an organic material to the surface of the lens. As an example, U.S. Pat. No. 3,916,033 (Merrill) discloses a method wherein a contact lens formed of a silicone polymer or copolymer is contacted with a liquid solution including a hydrophilic monomer. The surface is then exposed to ionizing radiation to form a hydrophilic polymer grafted on the lens surface. As a further example, U.S. Pat. No. 5,135,297 (Valint, Jr.) discloses a method wherein a contact lens is immersed in an aqueous dispersion of a polymerizable surfactant, a crosslinking agent and a free-radical initiator, and then exposed to ultraviolet radiation to form a crosslinked surface coating on the object.

In such surface treatments, the degree and uniformity of the bonding or grafting of the reactive material to the lens surface may be difficult to control. For example, in large-scale production, the coating may vary among individual lenses.

SUMMARY OF THE INVENTION

The invention relates to an improved method of treating RGP contact lenses, especially rigid, gas permeable contact lenses. The method comprises irradiating the contact lens with high energy radiation while the contact lens is immersed in an aqueous medium, wherein the aqueous medium excludes organic materials reactive with the contact lens surface. According to preferred embodiments, the medium is a saline solution or distilled water.

The method improves surface wettability of the treated RGP contact lens. Additionally, the method can be used to simultaneously sterilize and increase surface wettability of the treated lens. According to preferred embodiments, the treatment also improves dimensional stability of the contact lens and reduces the amount of residual, unreacted monomer.

This method provides higher predictability and uniformity of the treated lenses than the aforementioned surface techniques that involve forming a surface coating or bonding or grafting an organic material to the lens surface.

DETAILED DESCRIPTION OF THE INVENTION

The lenses treated by the method are conventional RGP contact lenses. Conventional RGP materials for contact lenses are well known in the art and include silicone acrylate copolymers and fluorosilicon acrylate copolymers. Representative silicone acrylate RGP materials include copolymers of a siloxane (meth)acrylate monomer (such as tris(trimethylsiloxy)silylpropyl methacrylate), a hydrophilic wetting monomer (such N-vinyl pyrrolidone or methacrylic acid), a crosslinking monomer (such as monomers having two terminal (meth)acrylate radicals), and a hardening monomer (such as methyl methacrylate or dimethyl itaconate). Fluorosilicon acrylate RGP materials include a fluorinated comonomer, for example, a fluorinated (meth)acrylate or fluorinated itaconate comonomer is included in place of, or in addition to, the nonfluorinated hardening monomer. Representative RGP materials are disclosed in U.S. Pat. Nos. 4,152,508 (Ellis et al.), 3,808,178 (Gaylord), 4,686,267 (Ellis et al.) and 4,780,515 (Deichert).

A critical feature of the invention is that the irradiation process is conducted on a contact lens having a desired final shape. Whereas the irradiation in the process disclosed in the aforementioned U.S. Pat. No. 4,330,383 may be performed on rods or buttons of the copolymeric material, which are then cut into lenses, the desired improvement in surface properties attributed to the present invention requires that the material is already in the desired contact lens shape during the irradiation process in order to obtain the desired improvement in surface properties.

An additional critical feature is that the lens is immersed in an aqueous medium during irradiation in order to obtain the desired improvement in surface properties.

The medium in which the contact lens is immersed is an aqueous medium. The medium can be based on water alone, or a solution such as saline solution can be used, including a buffered saline solution having a pH of about 7.1 to about 7.4. As discussed below, the method can further provide sterilization of the lens, so the use of saline avoids the need to use fresh buffered saline for packaging the treated lens. Additionally, RGP contact lenses generally cannot be sterilized by autoclaving, as used for soft hydrophilic contact lenses. Accordingly, a further feature of the invention is the provision of sterile, pre-wet, packaged RGP lenses ready for placement on the eye.

Since it is not a feature of the invention to form a surface coating on the treated contact lens, the medium in which the lens is immersed excludes organic materials reactive with the contact lens surface, especially organic monomeric materials.

Contact lenses are treated by immersing the contact lens in the aqueous medium, and irradiating the immersed lens with high energy radiation. A suitable container for the lens and medium during the irradiation is, for example, a glass vial such as PYREX brand glass.

As used herein, the term "high energy radiation" denotes radiation in the form of gamma rays, accelerated electrons, neutron particles, or alpha particles. Generally, the high energy radiation has an energy per particle or per quantum of from about $15 \times 10^6$ electron volts (15 Mev) to about 0.003×10⁶ electron volts (0.003 Mev). Several known high energy radiation sources are listed below.

| Radiation | Wavelength ($1 \times 10^{-10}$ m) | Energy per Particle (or per quantum, Mev) |
|---|---|---|
| x-rays | 0.008 to 40 | 1.5 to 003 |
| gamma rays | 0.0014 to 1.6 | 9 to 0.008 |
| accelerated electrons | 0.05 to 0.0008 | 15 to 0.25 |
| neutron particles | 0.05 to 0.0008 | 15 to 0.25 |
| alpha particles | 0.05 to 0.0008 | 15 to 0.25 |

The dosage of the high energy radiation is preferably chosen to effect sterilization and to improve dimensional stability, in addition to providing the improved surface properties, of the treated lens.

When using gamma rays, the absorbed dosage is preferably in the range of from 0.005 Megarads to 10 Megarads, and more preferably in the range of from 1 to 4 Megarads. When using x-rays, the absorbed dosage is preferably within the ranges given for gamma rays, and when using electron beam irradiation, the absorbed dosage is preferably in the range of from 0.005 Megarad to 1 Megarad. Sources for gamma radiation include conventional sources based on cobalt-60 or cesium-137, and many x-ray sources are available. If it is desired to effect sterilization during irradiation, it is preferred that the absorbed dosage is at least about 2.5 Megarads.

The time of exposure to irradiation may vary depending on the particular contact lens material and the type of irradiation, but can be optimized by one skilled in art through routine testing.

The following examples illustrate various preferred embodiments of the present invention.

EXAMPLE 1

Each of Batches A-1 and A-2 was composed of four contact lenses formed of a commercial fluorosilicon acrylate RGP material. Each of Batches B-1 and B-2 was composed of four contact lenses formed of a modified fluorosilicon acrylate material lacking wetting monomers.

Individual lenses were immersed in either distilled water or saline in glass vials. The vials and immersed lenses were subjected to 3.0 Megarads of gamma irradiation. For comparative purposes, four lenses of each material were placed in a sealed jar under a nitrogen atmosphere and subjected to 3.0 Megarads of gamma irradiation (designated A-Comp and B-Comp in Table 1).

Dynamic contact angle (DCA) measurements were made on each lens prior to and following irradiation using a Cahn Instruments DCA 322 at room temperature. Average advancing contact angles (Adv Ø) and receding contact angles (Rec Ø) were obtained from the DCA measurements. The results are reported in Table 1.

Additionally, the base curves of the lenses in Batches A-1, A-2, B-1 and B-2 were measured prior to and following irradiation to assess the effect of the treatment process on the dimensional stability of the lenses. The results are reported in Table 2.

TABLE 1

| Sample | Medium | Before Irradiation | | After Irradiation | |
|---|---|---|---|---|---|
| | | Adv Ø | Rec Ø | Adv Ø | Rec Ø |
| A-1 | dH₂O | 100 | 36 | 92 | 23 |
| A-2 | saline | 100 | 35 | 98 | 27 |
| A-Comp | N₂ | 101 | 37 | 100 | 37 |
| B-1 | dH₂O | 106 | 62 | 100 | 30 |
| B-2 | saline | 107 | 63 | 105 | 40 |
| B-Comp | N₂ | 107 | 61 | 105 | 60 |

TABLE 2

| Sample | Base Curve Change ($10^{-2}$ mm) |
|---|---|
| A-1 | 1 |
| A-2 | 0 |
| B-1 | 0 |
| B-2 | 1 |

The reduction in DCA, as summarized in Table 1, demonstrates that the process of the invention significantly improved surface wettability of the treated lenses. The data summarized in Table 2 demonstrates that the process provided lenses with satisfactory dimensional stability.

EXAMPLE 2

RGP lenses, or RGP wafers (0.2–0.3 mm thickness), made of the material used for Batches B-1 and B-2 in Example 1, were irradiated according to the general procedure of Example 1 followed by rubbing the irradiated sample with an abrasive-containing RGP cleaning composition. DCA measurements were made on the samples prior to irradiation, following irradiation and following cleaning. The data is summarized in Table 3.

TABLE 3

| Sample | Medium | Before Irradiation | | After Irradiation | | After Cleaning | |
|---|---|---|---|---|---|---|---|
| | | Adv Ø | Rec Ø | Adv Ø | Rec Ø | Adv | Rec |
| Wafer | dH₂O | 104 | 63 | 95 | 31 | 105 | 65 |
| Wafer | saline | 104 | 64 | 103 | 41 | 103 | 63 |
| Lens | dH₂O | 106 | 62 | 100 | 30 | 106 | 61 |
| Lens | saline | 107 | 63 | 105 | 40 | 105 | 63 |

It was found that the surface wettability of the samples following rubbing with the abrasive cleaner was comparable to that prior to the irradiation treatment, indicating that the modification of the lenses is limited to the lens surfaces.

Although certain preferred embodiments have been described, it is understood that the invention is not limited thereto and modifications and variations would be evident to a person of ordinary skill in the art.

We claim:

1. A method of increasing surface wettability of a rigid, gas permeable contact lens comprising irradiating a rigid, gas permeable contact lens with high energy radiation while the contact lens is immersed in an aqueous medium, wherein the medium excludes organic materials reactive with a surface of said contact lens.

2. The method of claim 1, wherein the radiation is gamma radiation.

3. The method of claim 1, wherein the medium consists essentially of water and sodium chloride.

4. The method of claim 1, wherein the medium is a saline solution.

5. The method of claim 4, wherein the medium is a buffered saline solution.

6. The method of claim 1, wherein the medium consists of distilled water.

7. A method of simultaneously sterilizing and increasing surface wettability of a RGP contact lens comprising irradiating a RGP contact lens with gamma irradiation while the contact lens is immersed in an aqueous medium, wherein the medium excludes organic materials reactive with a surface of said contact lens.

8. The method of claim 7, wherein the gamma irradiation is at least about 2.5 Megarads.

9. The method of claim 7, wherein the medium consists essentially of water and sodium chloride.

10. The method of claim 7, wherein the medium is a saline solution.

11. The method of claim 14, wherein the medium consists of distilled water.

12. A method of sterilizing, improving dimensional stability and increasing surface wettability of a rigid, gas permeable contact lens comprising irradiating a rigid, gas permeable contact lens with high energy irradiation while the contact lens is immersed in an aqueous medium, wherein the medium excludes organic materials reactive with surfaces of said contact lens.

13. The method of claim 12, wherein the medium is a saline medium.

14. The method of claim 12, wherein the medium consists of distilled water.

15. The method of claim 12, wherein the radiation is gamma irradiation.

* * * * *